United States Patent [19]

LeMahieu

[11] 4,168,380

[45] Sep. 18, 1979

[54] 7-METHOXY-5-OXO-5H-THIAZOLO[2,3-b]QUINAZOLINE-2-CARBOXYLIC ACID

[75] Inventor: Ronald A. LeMahieu, North Caldwell, N.J.

[73] Assignee: Hoffmann-La Roche Inc., Nutley, N.J.

[21] Appl. No.: 898,344

[22] Filed: Apr. 21, 1978

[51] Int. Cl.$^2$ .................. C07D 513/14; A61K 31/505
[52] U.S. Cl. ..................................... 544/250; 424/251
[58] Field of Search ......................... 544/250; 424/251

[56] References Cited

U.S. PATENT DOCUMENTS 4,083,980   4/1978   Schromm et al. ................... 424/251

FOREIGN PATENT DOCUMENTS 2557425   6/1977   Fed. Rep. of Germany .

OTHER PUBLICATIONS

Dhami et al., Chemical Abstracts, vol. 52, 5422f (1958).
Chemistry of Heterocyclic Compounds, "Fused Pyrimidines", Brown, ed. pp. 311–313, 319–320.

Primary Examiner—Donald G. Daus
Assistant Examiner—Diana G. Rivers
Attorney, Agent, or Firm—Jon S. Saxe; George M. Gould; William G. Isgro

[57] ABSTRACT

7-Methoxy-5-oxo-5H-thiazolo[2,3-b]quinazoline-2-carboxylic acid, useful as an antiallergic agent, and prepared by reaction of 5-methoxyanthranilic acid with methyl 2-chlorothiazole-5-carboxylate, and subsequent hydrolysis, is described.

1 Claim, No Drawings

7-METHOXY-5-OXO-5H-THIAZOLO[2,3-b]QUINAZOLINE-2-CARBOXYLIC ACID

BACKGROUND OF THE INVENTION

The invention relates to 7-methoxy-5-oxo-5H-thiazolo[2,3-b]quinazoline-2-carboxylic acid, characterized by the structure

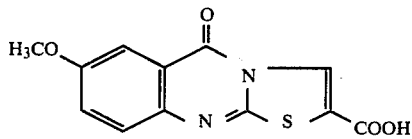   I

The compound of formula I is useful as an antiallergic agent.

DETAILED DESCRIPTION OF THE INVENTION

The compound of the invention, that is, 7-methoxy-5-oxo-5H-thiazolo[2,3-b]quinazoline-2-carboxylic acid, characterized by the formula

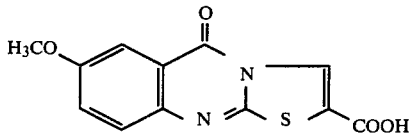   I can be prepared by condensing 5-methoxyanthranilic acid with a 2-halothiazole of the formula

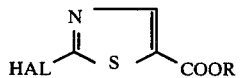   II wherein R is hydrogen or lower alkyl.
When R is hydrogen, the 7-methoxy-5-oxo-5H-thiazolo[2,3-b]quinazoline-2-carboxylic acid is recovered. When R is lower alkyl, an ester of the formula

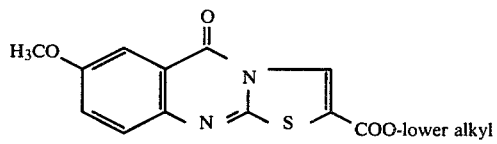   III is formed and is sequentially treated with a base and an acid to yield the desired 7-methoxy-5-oxo-5H-thiazolo[2,3-b]quinazoline-2-carboxylic acid.

The condensation of 5-methoxyanthranilic acid with the compound of formula II is carried out, preferably, at a temperature in the range of from about 150° to about 180° C. The condensation is usually carried out without added solvent. However, a high boiling polar solvent such as triglyme, dimethylformamide, or the like can be utilized. Furthermore, the condensation can be carried out with or without a catalyst. Exemplary of such catalysts are, for example, alkali metal iodides, such as sodium iodide, lithium iodide; preferably potassium iodide.

As used herein, the term "lower alkyl" denotes an alkyl radical of 1–7 carbon atoms such as methyl, ethyl, propyl, butyl and the like. The conversion of the ester of formula III to the desired acid, can be carried out in an excess of alkali metal hydroxide, for example, sodium hydroxide, potassium hydroxide, or the like, at a temperature preferably in the range of from about 0° to about 30° C. Most preferably, the reaction is carried out at about 25° C.

The hydrolysis is followed by refluxing with an organic carboxylic acid such as acetic acid, propionic acid, or the like. The desired 7-methoxy-5-oxo-5H-thiazolo[2,3-b]quinazoline-2-carboxylic acid can be recovered, in the process referred to above, utilizing conventional procedures such as recrystallization, or the like.

The compound of formula I forms salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium ethanolate, potassium ethanolate, and the like; organic bases such as piperidine, diethylamine, N-methylglucamine, and the like.

The compound of formula I, 7-methoxy-5-oxo-5H-thiazolo[2,3-b]quinazoline-2-carboxylic acid, and its pharmaceutically acceptable salts inhibit cutaneous anaphylaxis in rats, and are therefore useful in the prevention of allergic reactions, for example, they are useful in the prophylactic treatment of bronchial asthma. The anti-anaphylactic activity can be demonstrated by the passive cutaneous anaphylaxis assay (PCA test) in the rat. This test involves passive local sensitization of rats by intra-dermal injection of anti-sera. After a latent period of 24 hours, the test compound, in this case, 7-methoxy-5-oxo-5H-thiazolo[2,3-b]quinazoline-2-carboxylic acid, is given intraperitoneally followed after 5 minutes by an intravenous injection of reagin and Evans blue dye. The events associated with localized antigen-antibody reaction lead to the formation of skin wheals whose sizes are measured. The ability of the test compound to decrease the size of the wheals compared to controls is taken as a measure of its activity.

When 7-methoxy-5-oxo-5H-thiazolo[2,3-]quinazoline-2-carboxylic acid is utilized as the test compound at a dose of 16 mg/kg. intraperitoneally, the reduction in the wheal size is 100%.

When 7-methoxy-5-oxo-5H-thiazolo[2,3-b]quinazoline-2-carboxylic acid is utilized as the test compound at a dose of 0.07 mg/kg. orally, the reduction in the wheal size is 50%.

The 7-methoxy-5-oxo-5H-thiazolo[2,3-b] quinazoline-2-carboxylic acid and its pharmaceutically acceptable salts can be administered orally or parenterally as antiallergic agents, for example, in the prophylactic treatment of bronchial asthma, with dosage adjustments for individual requirements. They can be administered therapeutically, for example, orally or parenterally, by incorporating a therapeutic dosage in a conventional dosage form, such as tablets, capsules, elixirs, suspensions, solutions, aerosols or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity, and the pharmaceutical dosage forms can, if desired, be subjected to conventional pharmaceutical expedients such as, for example, sterilization. As stated above, the dosage can be adjusted to individual requirements. They can also contain other therapeutically valuable substances.

The quantity of active medicament which is present in any of the above-described dosage forms is variable. It is preferred, however, to provide capsules or tablets containing from about 10 mg. to about 20 mg. of 7-methoxy-5-oxo-5H-thiazolo[2,3-b]quinazoline-2-carboxylic acid or an equivalent amount of a medicinally acceptable acid addition salt thereof.

The frequency with which any such dosage form will be administered to a warm-blooded mammal will vary, depending upon the quantity of active medicament present therein and the needs and requirements of the warm-blooded mammal. Under ordinary circumstances, however, up to about 20 mg/kg. of 7-methoxy-5-oxo-5H-thiazolo[2,3-b] quinazoline-2-carboxylic acid can be administered daily in several dosages. It is to be understood, however, that the dosages set forth therein are exemplary only and that they do not, to any extent, limit the scope or practice of this invention.

As used herein, the term "HAL" denotes a halogen, such as, chlorine, bromine, fluorine or iodine.

The examples which follow further illustrate the invention.

EXAMPLE I

Preparation of Methyl 2-chlorothiazole-5-carboxylate

To 5.0 g of methyl 2-aminothiazole-5-carboxylate [H. E. Faith, U.S. Pat. No. 2,405,820(1946)] suspended in 54 ml of 6 N hydrochloric acid stirred at-5-0° was added dropwise over 15 minutes 3.7 g of sodium nitrite dissolved in 10 ml of water. After stirring 5 minutes, the brown suspension was added in one portion to a rapidly stirred suspension of 10.6 g of cupric sulfate and 10.6 g of sodium chloride cooled at 5°. The cooling bath was removed and stirring was continued for 30 minutes. The pH was adjusted to 7.3 with 6 N sodium hydroxide and the green suspension was filtered through Celite. The solid was washed with three portions of ethyl acetate and the extract was combined with the ethyl acetate extract of the original filtrate. After drying the combined extract over magnesium sulfate, concentration in vacuo gave a brown solid. Trituration with four portions of hot petroleum ether (35°–60°) served to separate the soluble product from some starting material. Concentration in vacuo of the petroleum ether solution gave 3.9 g. of pure methyl 2-chlorothiazole-5-carboxylate having a melting point of 41°–46°.

EXAMPLE 2

Preparation of 7-Methoxy-5-oxo-5H-thiazolo[2,3-b]quinazoline-2-carboxylic acid

An intimate mixture of 1.49 g of 5-methoxyanthranilic acid, 1.58 g of methyl 2-chlorothiazole-5-carboxylate and 0.075 g of powdered potassium iodide was stirred and heated in an oil bath at 160°–165° for 80 minutes. The resultant dark solid was treated with 75 ml of a saturated solution of sodium bicarbonate and extracted with three portions of chloroform. The combined, dried (over magnesium sulfate) extract was concentrated in vacuo to a tan solid (1.59 g). Crystallization from methylene chloride-ether gave 0.86 g of methyl 7-methoxy-5-oxo-5H-thiazolo[2,3-b]quinazoline-2-carboxylate, having a melting point of 186°–192° C. This methyl ester was hydrolyzed by stirring for 16 hours at room temperature with 30 ml of 1 N sodium hydroxide and 30 ml of methanol. After filtration, the filtrate was acidified with acetic acid to pH5 and concentrated in vacuo. Water was added and the solid was removed by filtration. Since the base treatment also opens the lactam, this solid was refluxed for 1 hour in 75 ml of acetic acid. After concentration to 25 ml, the product crystallized on cooling and was filtered to give 0.53 of pure 7-methoxy-5-oxo-5H-thiazolo[2,3-b]quinazoline-2-carboxylic acid having a melting point of 247°–247.5° C.

EXAMPLE 3

| Capsule Formulation | | |
|---|---|---|
| | mg/capsule | |
| | 10 mg | 20 mg |
| 7-Methoxy-5-oxo-5H-thiazolo [2,3-b] quinazoline-2-carboxylic acid | 10.0 | 20.0 |
| Lactose | 215.0 | 205.0 |
| Cornstarch | 60.0 | 60.0 |
| Magnesium Stearate | 3.0 | 3.0 |
| Talc | 12.0 | 12.0 |
| Total | 300 mg. | 300 mg. |

Procedure:

Mix 7-methoxy-5-oxo-5H-thiazolo[2,3-b]quinazoline-2-carboxylic acid, lactose and cornstarch in a suitable mixer. Mill through suitable mill. Mix with magnesium stearate and talc and fill on capsule machine.

EXAMPLE 4

| Tablet Formulation | | |
|---|---|---|
| | mg/tablet | |
| | 10 mg. | 20 mg. |
| 7-methoxy-5-oxo-5H-thiazolo [2,3-b]quinazoline-2-carboxylic acid | 10.0 | 20.0 |
| Lactose | 182.0 | 172.0 |
| Microcrystalline Cellulose | 60.0 | 60.0 |
| Modified Starch | 15.0 | 15.0 |
| Cornstarch | 30.0 | 0.0 |
| Magnesium Stearate | 3.0 | 3.0 |
| Total | 300 mg | 300 mg |

Procedure:

Mix 7-methoxy-5-oxo-5H-thiazolo[2,3-b]quinazoline-2-carboxylic acid, lactose, microcrystalline cellulose, modified starch and cornstarch in a suitable mixer for 1 to 15 minutes. Then, add magnesium stearate and mix for 5 minutes. Compress on a suitable press.

EXAMPLE 5

| Wet Granulation Tablet Formulation | | |
|---|---|---|
| | mg/tablet | |
| | 10 mg | 20 mg |
| 7-methoxy-5-oxo-5H-thiazolo [2,3-b]quinazoline-2-carboxylic acid | 10.0 | 20.0 |
| Lactose | 264.0 | 254.0 |
| Pregelatinized Starch | 17.5 | 17.5 |
| Cornstarch | 35.0 | 35.0 |
| Modified Starch | 17.5 | 17.5 |
| Magnesium Stearate | 6.0 | 6.0 |
| Total | 350 mg. | 350 mg. |

Procedure:

Mix 7-methoxy-5-oxo-5H-thiazolo[2,3-b]quinazoline-2-carboxylic acid, lactose, corn starch and pregelatinized starch in a suitable mixer. Granulate with water. Mill through suitable mill. Mix with modified starch and magnesium stearate and compress on a suitable tablet press.

I claim:

1. 7-Methoxy-5-oxo-5H-thiazolo[2,3-b]quinazoline-2-carboxylic acid.